United States Patent

Guracar

(10) Patent No.: US 8,316,714 B2
(45) Date of Patent: Nov. 27, 2012

(54) SCAN PATTERNS FOR ELECTRONICALLY POSITIONED APERTURES ON AN ARRAY

(75) Inventor: Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 285 days.

(21) Appl. No.: 12/780,688

(22) Filed: May 14, 2010

(65) Prior Publication Data

US 2011/0016977 A1  Jan. 27, 2011

Related U.S. Application Data

(60) Provisional application No. 61/227,639, filed on Jul. 22, 2009.

(51) Int. Cl.
*G01N 29/04* (2006.01)
*G06F 19/00* (2006.01)

(52) U.S. Cl. .............. 73/606; 73/618; 702/56

(58) Field of Classification Search .......... 73/606, 73/607, 609, 618, 625–626; 600/437, 441, 600/443, 447; 702/56
See application file for complete search history.

(56) References Cited

U.S. PATENT DOCUMENTS

| | | | |
|---|---|---|---|
| 6,676,602 B1 | 1/2004 | Barnes et al. | |
| 6,836,159 B2 | 12/2004 | Wodnicki | |
| 7,207,943 B2 * | 4/2007 | Barnes et al. | 600/447 |
| 7,313,053 B2 | 12/2007 | Wodnicki | |
| 7,322,936 B2 * | 1/2008 | Takeuchi | 600/447 |
| 7,353,056 B2 | 4/2008 | Hazard et al. | |
| 7,635,334 B2 * | 12/2009 | Phelps | 600/447 |
| 7,658,713 B2 * | 2/2010 | Barnes et al. | 600/437 |
| 7,780,597 B2 * | 8/2010 | Panda et al. | 600/437 |
| 7,789,831 B2 * | 9/2010 | Barnes et al. | 600/437 |
| 7,798,967 B2 * | 9/2010 | Takeuchi | 600/447 |
| 7,963,919 B2 * | 6/2011 | Proulx et al. | 600/447 |
| 2002/0135415 A1 | 9/2002 | Dufort | |

OTHER PUBLICATIONS

Platt, John C., *Optimal Filtering for Patterned Displays*, IEEE Signal Processing Letters, vol. 7, No. 7, Jul. 2000, pp. 179-181.

* cited by examiner

*Primary Examiner* — J M Saint Surin (57) ABSTRACT

A plane or volume is scanned with ultrasound. Electronic movement of apertures is used during the scanning. Scanning with the apertures is interleaved. The apertures move along the array in opposite directions, preventing or limiting large temporal discontinuity. For example, two apertures begin at similar angles on a two-dimensional array. Planar scans are performed for each aperture location. The apertures are counter rotated (i.e., one clockwise and the other counter clockwise).

19 Claims, 3 Drawing Sheets

SCAN PATTERNS FOR ELECTRONICALLY POSITIONED APERTURES ON AN ARRAY

RELATED APPLICATIONS

The present patent document claims the benefit of the filing date under 35 U.S.C. §119(e) of Provisional U.S. Patent Application Ser. No. 61/227,639, filed Jul. 22, 2009, which is hereby incorporated by reference.

BACKGROUND

The present embodiments relate to ultrasound imaging. In particular, the present embodiments relate to scanning with an electronically positioned aperture on an array.

An electronically rotated array is an array of elements where the aperture used during scanning is electronically controlled. Switches connect different elements to different beamformer channels, allowing rotation of the aperture for sequential scanning. For example, a one-dimensional aperture is rotated electronically on the face of a two-dimensional transducer array. By controlling the configuration of the switches, the one-dimensional array may be oriented to any rotational angle. Within a given aperture, the defined one-dimensional array may steer scan lines to ±45°, allowing an acoustic transmit and receive beam to be focused anywhere within a 90° cone extending out from the face of the transducer through scan line steering and aperture rotation. For volume scanning, the 90° cone in space is sampled by collecting a series of azimuth-spaced beam groups at each rotation angle.

One significant artifact caused by the sampling scheme described above in the presence of tissue motion is a large time gap in acquiring spatially adjacent rotation angle slices. If the scanning starts at the aperture rotation angle zero and then the remaining angle slices are acquired to complete a group of 60 scan planes with corresponding aperture locations, the first rotation angle at 0° is reconstructed adjacent in space to the angle slice with a rotation angle of 177°, even though they are acquired many transmit events apart in time. If there is significant motion, there may be a large discontinuity or "seam" in the reconstructed volume image.

To increase frame rate, data for additional scan lines may be interpolated from actual receive data. This analytic operation may be performed for scan lines in different apertures. Where a relatively large amount of time separates the acquisition between the two apertures, interpolation artifacts may be produced due to phase cancellation caused by motion.

BRIEF SUMMARY

The present invention is defined by the following claims, and nothing in this section should be taken as a limitation on those claims. By way of introduction, the preferred embodiments described below include methods and systems for scanning with ultrasound. A plane or volume is scanned with electronic movement of apertures. Scanning with the apertures is interleaved. The apertures move along the array in opposite directions, preventing or limiting large temporal discontinuity. For example, two apertures begin at similar angles on a two-dimensional array. Planar scans are performed for each aperture location. The apertures are counter rotated (i.e., one clockwise and the other counter clockwise).

In a first aspect, a method for scanning within a three-dimensional volume is provided. A plurality of different one-dimensional apertures is defined on a multidimensional array. Each of the different one-dimensional apertures corresponds to a different rotation angle relative to the multidimensional array. The three-dimensional volume is scanned with ultrasound sequentially from the different one-dimensional apertures at the different rotation angles. The scanning is performed with a counter rotation sequence of the different one-dimensional apertures corresponding to two or more rotating aperture groups of the different one-dimensional apertures sequentially rotating in opposite directions.

In a second aspect, a tangible computer readable storage medium has stored therein data representing instructions executable by a programmed processor for scanning with ultrasound. The storage medium includes instructions for scanning along a plurality of scan lines in a sequence where the scan lines of the sequence form a continuous region, forming a plurality of different apertures in an array of elements for the scanning, the different apertures corresponding to different scan lines and stepped through the continuous region such that each aperture has at least two apertures on opposite sides, and using an interleaved sequence of the different apertures for the scanning, the interleaved sequence stepping the different apertures in opposite directions along the array of elements through the sequence.

In a third aspect, a system is provided for scanning with ultrasound. A beamformer connects with an array of acoustic transducer elements array. The beamformer is configured to interleave two moving apertures on the array. The two moving apertures move in different directions such that adjacent locations for the moving apertures are separated by five or fewer scans using other locations of the moving apertures. A detector is configured to detect data output by the beamformer and responsive to the moving apertures. A display is configured to generate an image from the detected data.

Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Electronically rotatable one-dimensional ultrasound arrays may provide a simplified and low cost real-time three-dimensional volume acquisition suitable for cardiac imaging. Fewer beamforming channels may be needed than scanning with a fully sampled two-dimensional array.

For the scan, acquisition sequences and signal processing may be applied to minimize artifacts due to motion and maximize image information content and quality. Multiple rotation angle sequences are interleaved to minimize time gaps between adjacent lateral block groups.

Any real-time ultrasound volume or plane imaging system may use oppositely moving apertures to reduce temporal discontinuity. For example, this enables the use of a relatively simple, electronically steered 1-D array with a 2D beamformer to produce a collection of 2D images, which can be combined to produce real time volume images with reduced temporal artifacts.

The frame or volume scan rate may be increased by variation of scan line density. In the rotating aperture example, the density of samples varies as a function of lateral block group and rotation angle. Analytic interpolation is used to increase the sampling density prior to detection for missing data.

Figure 1:
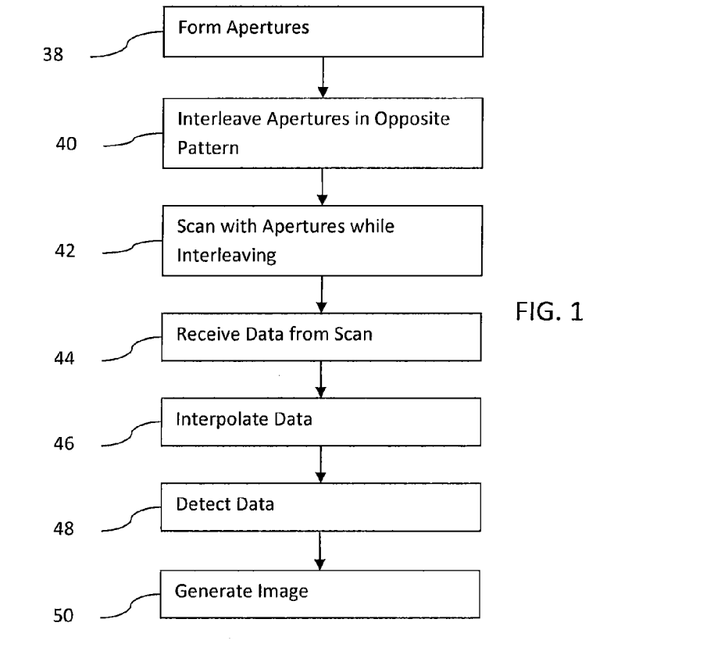
FIG. 1 is a flow chart diagram of one embodiment of a method for scanning with ultrasound.

FIG. 1 shows a method for scanning with ultrasound. In one example embodiment, scanning within a three-dimensional volume is provided. In other embodiments, the scanning is of a plane, such as associated with a ring of elements in an array around an entire circumference. The method is implemented using the system of FIG. 5 or a different system. The method is performed in the order shown or a different order. Additional, different, or fewer acts may be provided. For example, acts 44, 46, 48, and/or 50 are not provided or provided in non-real time.

In act 38, a plurality of different apertures is formed in an array of elements. The apertures are formed by switching, such as one or more switches for each element connecting the elements together and/or to beamformer channels. For example, the switching and arrays described in U.S. Pat. No. 6,676,602, the disclosure of which is incorporated herein by reference, is used. As another example, beamformer channels are connected to elements by two layers of switches, one layer having a channel matrix interconnected laterally and another layer having an acoustic element matrix interconnected to the channel matrix along another direction. Alternatively, one or more beamformer channels are turned on or off to include or not include a connected element in the aperture. Other aperture selections may be used.

Each aperture includes one or more elements. For example, the apertures are one-dimensional. The aperture is formed from a plurality of elements along a straight or curved line. In other embodiments, the apertures are multi-dimensional, such as having a 1.25D, 1.5D, or 1.75D arrangement of two or more rows of elements.

The switches or beamformer operation forming the aperture at a given time are configured to switch quickly, allowing real-time aperture change or operation free of mechanical movement. Electronic switching may occur more rapidly than mechanical movement. Any type of switch may be used for electronic movement of the aperture.

Each aperture is at a different position on an array. The aperture may slide along an array. For example, the aperture is translated laterally or in azimuth along an array of elements. As another example, the aperture rotates across the face of a multi-dimensional array. The rotation is about a center or other location on the multi-dimensional array, but may be about a point spaced from the face of the array. Each aperture is rotated by a different amount. In another example, the aperture translates laterally in elevation across a multi-dimensional array. Combinations of translation and rotation may be used. Each translated or rotated location corresponds to another aperture. The apertures in sequence correspond to a given aperture being translated or rotated to the different locations.

Any step size for the translation and/or rotation may be used. The step size is the same between each aperture location. For example, equal amounts of rotation are provided for each aperture location. In alternative embodiments, the step size for rotation and/or translation may vary, such as having a smaller step size to more heavily sample one region over another or to reduce frame rate by providing lesser sampling for some regions.

In one embodiment, the apertures are located such that the beams or scan planes overlap or are adjacent to each other, forming a continuous region being scanned. Similarly, the aperture positions are adjacent to each other or overlap within the array (i.e., share elements). Given acoustic divergence, the apertures for scanning a continuous region may be spatially separated by one or more elements with a corresponding region near the aperture which is not scanned. The region is continuous by being interconnected between all of the scan regions associated with all of the apertures. For any given aperture location, another of the aperture locations is provided on each side (e.g., each aperture has at least two other ones of the apertures on opposite sides). The region may be continuous by being circular, such as scanning a plane with a ring array such that there is no lateral beginning or ending (i.e., no lateral edge). The aperture steps through a sequence in a continuous loop with a same or similar step size. The edge is only along the depth dimension. The region may be continuous by being associated with rotation of the aperture, such that the outside lateral scan lines form one edge along a curved surface of the continuous region and the depth forms another edge. Each aperture has at least two other of the apertures on opposite sides. The region may be continuous by being associated with translation of the aperture, such that a flat outside edge is provided as well as a depth edge. In this case, the apertures at the elevation edges do not have apertures on opposite sides. In alternative embodiments, a gap or region not being scanned is provided between apertures or the region being scanned.

For scanning, the different apertures correspond to different scan line positions. For example, the aperture is a one-dimensional aperture used to scan a plane. Scan lines in a sector, Vector™, linear or other format are used for scanning at the aperture location. The format is repeated at other aperture locations for other scan lines in the continuous region.

In act 40, an interleaved sequence of the different apertures is used for scanning. Two or more apertures are moved during the scanning. The aperture locations are grouped into two or more sets, each set providing the locations of apertures making up a given aperture movement. The scanning is interleaved between the sets, such as forming an aperture at one location for set 1, then forming an aperture at another location for set 2, then forming yet another location for set 1, and so on. Multiple apertures may be scanned from a given set before interleaving or switching to the apertures of another set. The order of the apertures within each set is arranged to reduce or minimize the amount of time between scanning adjacent portions of the scan region.

The different apertures are moved relative to each other as part of the interleaving. The interleaving of apertures may use various array topologies for either two- or three-dimensional imaging. For example, the interleaved sequence steps the different apertures in opposite directions along the array of elements through the sequence. For a one-dimensional ring array, one aperture steps clockwise around the one-dimensional ring array and another aperture steps counter-clockwise around the one-dimensional ring array. The ring array may be used in a catheter or around another circumference to sample a two-dimensional image slice. Small groups of elements are sequentially recruited to acquire lines around the ring. When the last line is scanned, there is a temporal seam in the reconstructed image between the first and last acquired line. Use of counter rotating interleaved angle sequences may remove the large time gap between these adjacent acquired lines. For example, one aperture starts at zero degrees and the other aperture starts at 178 degrees. Interleaving in an every other manner between these two apertures provides for little delay between adjacent apertures. The zero degree aperture is translated to 2 degrees, and the 178 degree aperture is translated to 176 degrees. By interleaving, a larger but still small temporal gap is provided between the apertures within each group (i.e., 178-90 and 0-88 groups).

In another possible use, a single helical array or series of helical arrays are arranged to allow volume scanning over a complete 360 degree cylinder. The apertures are arranged in oppositely translating and/or rotating groups. The scanning is interleaved between the groups.

Figure 2:
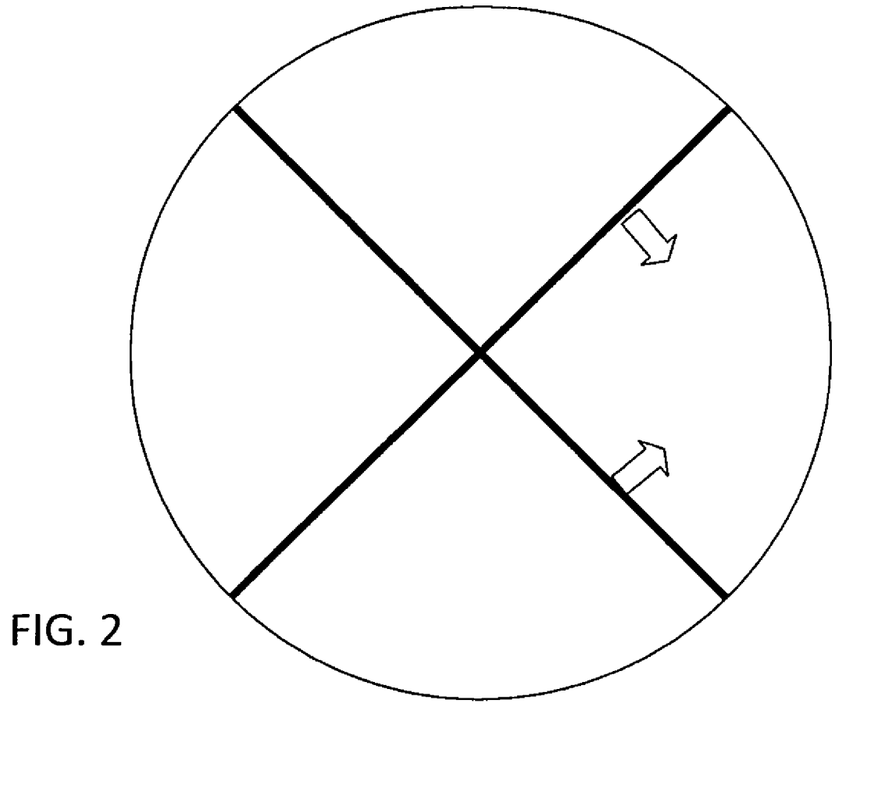
FIG. 2 is a graphical illustration of two counter-rotating apertures according to one example.

In another embodiment, apertures are rotated about a face of a multi-dimensional array. For example, one aperture steps clockwise around a center of rotation or the array, and another aperture steps counter-clockwise around the center of rotation. FIG. 2 shows this embodiment. This counter rotation is interleaved. The scanning is performed with a counter rotation sequence of the different apertures. The rotation is in opposite directions. The counter rotating apertures are sequentially rotated and used for scanning.

More than two sets of apertures may be used, such as four counter rotating apertures. For two sets of aperture locations, each set is formed from every other location. Other groupings may be provided, such as every N aperture locations where N is a positive integer. For four sets of aperture locations, the aperture locations are divided into two contiguous groups, such as 0-89 degrees and 90-180 degrees. Each group is then divided amongst two sets, such as divided into every other location within the group.

Rather than acquiring rotation angle slices in a continuously ascending rotation angle sequence, the sequence is modified to contain interleaved counter-rotating sequences. Example conventional and new sequences are shown in Table 1. In the 2-way interleaved sequence case, two counter-rotating sequences are time interleaved. The first sequence starts at 0 degrees and increments by 3 degrees. The second sequence starts at 177 degrees and decrements by 3 degrees. In the 4-way example, the first interleaved sequence starts at 0 degrees and increments by 3 degrees. The second interleaved sequence starts at 90 degrees and also increments. The third starts at 87 degrees and decrements by 3 degrees. The fourth starts at 177 degrees and also decrements.

TABLE 1

| Rotation sequence | Conventional rotation angle | 2-way rotation angle | 4-way rotation angle |
|---|---|---|---|
| 1 | 0° | 0° | 0° |
| 2 | 3 | 177 | 90 |
| 3 | 6 | 3 | 87 |
| 4 | 9 | 174 | 177 |
| 5 | 12 | 6 | 3 |
| 6 | 15 | 171 | 93 |
| 7 | 18 | 9 | 84 |
| 8 | 21 | 168 | 174 |
| 9 | 24 | 12 | 6 |
| 10 | 27 | 165 | 96 |
| 11 | 30 | 15 | 81 |
| 12 | 33 | 162 | 171 |
| 13 | 36 | 18 | 9 |
| 14 | 39 | 159 | 99 |
| 15 | 42 | 21 | 78 |
| 16 | 45 | 156 | 168 |

TABLE 1-continued

| Rotation sequence | Conventional rotation angle | 2-way rotation angle | 4-way rotation angle |
|---|---|---|---|
| 17 | 48 | 24 | 12 |
| 18 | 51 | 153 | 102 |
| 19 | 54 | 27 | 75 |
| 20 | 57 | 150 | 165 |
| 21 | 60 | 30 | 15 |
| 22 | 63 | 147 | 105 |
| 23 | 66 | 33 | 72 |
| 24 | 69 | 144 | 162 |
| 25 | 72 | 36 | 18 |
| 26 | 75 | 141 | 108 |
| 27 | 78 | 39 | 69 |
| 28 | 81 | 138 | 159 |
| 29 | 84 | 42 | 21 |
| 30 | 87 | 135 | 111 |
| 31 | 90 | 45 | 66 |
| 32 | 93 | 132 | 156 |
| 33 | 96 | 48 | 24 |
| 34 | 99 | 129 | 114 |
| 35 | 102 | 51 | 63 |
| 36 | 105 | 126 | 153 |
| 37 | 108 | 54 | 27 |
| 38 | 111 | 123 | 117 |
| 39 | 114 | 57 | 60 |
| 40 | 117 | 120 | 150 |
| 41 | 120 | 60 | 30 |
| 42 | 123 | 117 | 120 |
| 43 | 126 | 63 | 57 |
| 44 | 129 | 114 | 147 |
| 45 | 132 | 66 | 33 |
| 46 | 135 | 111 | 123 |
| 47 | 138 | 69 | 54 |
| 48 | 141 | 108 | 144 |
| 49 | 144 | 72 | 36 |
| 50 | 147 | 105 | 126 |
| 51 | 150 | 75 | 51 |
| 52 | 153 | 102 | 141 |
| 53 | 156 | 78 | 39 |
| 54 | 159 | 99 | 129 |
| 55 | 162 | 81 | 48 |
| 56 | 165 | 96 | 138 |
| 57 | 168 | 84 | 42 |
| 58 | 171 | 93 | 132 |
| 59 | 174 | 87 | 45 |
| 60 | 177 | 90 | 135 |

Other groups, sets, sequences, step sizes, number of locations, or configurations may be used.

In act 42, the apertures are used for scanning. One or more scan lines are formed for each aperture location or aperture. In the embodiment with a one-dimensional array for each aperture, a plurality (e.g., tens or hundreds) of scan lines are scanned.

Scanning is performed by beamformation. Relative delays and/or apodization determine the scan line origin and angle. For a one-dimensional array, the angle is an azimuth angle relative to the aperture. Acoustic energy is transmitted along the scan line. Receive beamformation samples the echoes from the transmitted acoustic energy along the same or a different scan line. In one embodiment, one scan line is used for each transmit and receive event. In another embodiment, the transmitted acoustic energy has a beam width in azimuth for receiving along two or more scan lines simultaneously or in response to the same transmitted beam. For example, eight receive beams are formed for each transmit beam. A fewer or larger number of receive beams may be formed for a given transmit event.

By scanning with a plurality apertures at different locations, a volume is scanned in one embodiment. A planar scan is provided in another embodiment, such as with the ring array. By scanning along a plurality of scan lines in a sequence, the continuous region may be sampled.

For the volume scan, the three-dimensional volume is scanned with ultrasound sequentially from the different one-dimensional or other apertures at different rotation angles and/or translations. In one embodiment, each aperture is used for scanning a plane. A two-dimensional beamformer may be used to sequentially scan a volume without the need for additional beamformer channels. For example, seven transmit events are performed for each plane or aperture. The transmit events have about 13 degree spacing to collect information for an about 90 degree sector or Vector™ scan for a given rotation angle slice. Multibeam receive samples the receive beam using 8-beams spaced about 1.6 degrees apart for each transmit beam. Combined, a scan of a planar slice uses 56 receive lines. Using sixty rotation angle slices or apertures spaced about 3 degrees apart, the contiguous volume region is scanned. The receive samples are combined into a data set or collected to sample the complete space over a full 180 degree rotation space. Sixty rotation angle slices by 7 transmit events requires 420 transmit events. If the depth to be samples is about 150 mm, requiring about 200 μsec of round trip sound transit time, the volume sampling rate is about 12 Hz. This rate provides for visually acceptable real-time imaging while scanning. One example is given above. Different numbers of receive beams per transmit beam, number of transmit beams per plane or aperture, number of apertures, depths, or other values may be used.

The interleaving of the scanning results in time gaps between scanning for sequential ones of the different one-dimensional apertures. A normalized time gap of one is provided between each aperture, assuming a same format and extent of scan is performed for each aperture. Since scanning is interleaved between two or more groups or sets of apertures, the time gap between adjacent apertures may be greater than one. For example, every other aperture interleaving (2-way in table 1) is performed for two moving apertures or sets of apertures. The scans for each adjacent one of the different one-dimensional apertures are temporally separated by two of the time gaps. Where the interleaving is performed with two or more scans for a given set occurring before changing to scanning from the other group, some of the scans may be separated by a time gap of one. In the 4-way embodiment, the scans for adjacent apertures are temporally separated by four of the time gaps or less given every aperture interleaving.

Imaging dynamic objects, such as the heart, with a conventional scanning sequence may produce motion artifacts at the seam. For example using the rotating one-dimensional array, a conventional scan may start with an aperture at 0 degrees and step the aperture through to 180 degrees. The apertures between 0 and 180 degrees have a large temporal gap, creating a seam. The use of the counter-rotating interleaved angle sequences may remove the large time gap between adjacent acquired image planes or regions and avoid the temporal discontinuity artifact in the reconstructed image.

All adjacent rotation angle slices are acquired with relatively small and uniform time gaps using two or more groups of apertures with interleaved, opposite steps or scanning sequences through the groups. There is no large time gap between any pair of slices in the one-dimensional rotating array embodiment. This is contrasted with the very large gap between the conventional sequence between rotation angle of 0° and 177°. The time gaps between slices at a given rotation angle and the previous angle are shown in Table 2 for the same example cases above.

TABLE 2

Time gaps as a function of rotation angle

| rotation angle | Conventional | | 2-way case | | 4-way case | |
|---|---|---|---|---|---|---|
| | Seq. | Time Gap | Seq. | Time Gap | Seq. | Time Gap |
| 0° | 1 | 59 | 1 | 1 | 1 | 3 |
| 3 | 2 | 1 | 3 | 2 | 5 | 4 |
| 6 | 3 | 1 | 5 | 2 | 9 | 4 |
| 9 | 4 | 1 | 7 | 2 | 13 | 4 |
| 12 | 5 | 1 | 9 | 2 | 17 | 4 |
| 15 | 6 | 1 | 11 | 2 | 21 | 4 |
| 18 | 7 | 1 | 13 | 2 | 25 | 4 |
| 21 | 8 | 1 | 15 | 2 | 29 | 4 |
| 24 | 9 | 1 | 17 | 2 | 33 | 4 |
| 27 | 10 | 1 | 19 | 2 | 37 | 4 |
| 30 | 11 | 1 | 21 | 2 | 41 | 4 |
| 33 | 12 | 1 | 23 | 2 | 45 | 4 |
| 36 | 13 | 1 | 25 | 2 | 49 | 4 |
| 39 | 14 | 1 | 27 | 2 | 53 | 4 |
| 42 | 15 | 1 | 29 | 2 | 57 | 4 |
| 45 | 16 | 1 | 31 | 2 | 59 | 2 |
| 48 | 17 | 1 | 33 | 2 | 55 | 4 |
| 51 | 18 | 1 | 35 | 2 | 51 | 4 |
| 54 | 19 | 1 | 37 | 2 | 47 | 4 |
| 57 | 20 | 1 | 39 | 2 | 43 | 4 |
| 60 | 21 | 1 | 41 | 2 | 39 | 4 |
| 63 | 22 | 1 | 43 | 2 | 35 | 4 |
| 66 | 23 | 1 | 45 | 2 | 31 | 4 |
| 69 | 24 | 1 | 47 | 2 | 27 | 4 |
| 72 | 25 | 1 | 49 | 2 | 23 | 4 |
| 75 | 26 | 1 | 51 | 2 | 19 | 4 |
| 78 | 27 | 1 | 53 | 2 | 15 | 4 |
| 81 | 28 | 1 | 55 | 2 | 11 | 4 |
| 84 | 29 | 1 | 57 | 2 | 7 | 4 |
| 87 | 30 | 1 | 59 | 2 | 3 | 4 |
| 90 | 31 | 1 | 60 | 1 | 2 | 1 |
| 93 | 32 | 1 | 58 | 2 | 6 | 4 |
| 96 | 33 | 1 | 56 | 2 | 10 | 4 |
| 99 | 34 | 1 | 54 | 2 | 14 | 4 |
| 102 | 35 | 1 | 52 | 2 | 18 | 4 |
| 105 | 36 | 1 | 50 | 2 | 22 | 4 |
| 108 | 37 | 1 | 48 | 2 | 26 | 4 |
| 111 | 38 | 1 | 46 | 2 | 30 | 4 |
| 114 | 39 | 1 | 44 | 2 | 34 | 4 |
| 117 | 40 | 1 | 42 | 2 | 38 | 4 |
| 120 | 41 | 1 | 40 | 2 | 42 | 4 |
| 123 | 42 | 1 | 38 | 2 | 46 | 4 |
| 126 | 43 | 1 | 36 | 2 | 50 | 4 |
| 129 | 44 | 1 | 34 | 2 | 54 | 4 |
| 132 | 45 | 1 | 32 | 2 | 58 | 4 |
| 135 | 46 | 1 | 30 | 2 | 60 | 2 |
| 138 | 47 | 1 | 28 | 2 | 56 | 4 |
| 141 | 48 | 1 | 26 | 2 | 52 | 4 |
| 144 | 49 | 1 | 24 | 2 | 48 | 4 |
| 147 | 50 | 1 | 22 | 2 | 44 | 4 |
| 150 | 51 | 1 | 20 | 2 | 40 | 4 |
| 153 | 52 | 1 | 18 | 2 | 36 | 4 |
| 156 | 53 | 1 | 16 | 2 | 32 | 4 |
| 159 | 54 | 1 | 14 | 2 | 28 | 4 |
| 162 | 55 | 1 | 12 | 2 | 24 | 4 |
| 165 | 56 | 1 | 10 | 2 | 20 | 4 |
| 168 | 57 | 1 | 8 | 2 | 16 | 4 |
| 171 | 58 | 1 | 6 | 2 | 12 | 4 |
| 174 | 59 | 1 | 4 | 2 | 8 | 4 |
| 177 | 60 | 1 | 2 | 2 | 4 | 4 |

Other sequences are possible. The rotation angle, slice acquisition sequence with oppositely moving apertures minimizes the time gap across the rotation angle slices. The time gap between most adjacent apertures may be larger (e.g., 2 or 4 instead of 1), but across the entire scan pattern the time gaps are more even and uniform (e.g., no 59 time gap between two apertures). The goal is a sequence that samples the space and allows scan lines for adjacent apertures to be acquired without a large time difference. This allows reconstruction for imaging without a large temporal discontinuity or "seam" in the image. The time gaps are evenly or substantially evenly (e.g., less than 100% variation) distributed.

The 2-way sequence provides a smaller time gap between slices and perhaps a simpler implementation due to less switching between beamformer channels and elements. Another difference between the interleave-by-2 and the interleave-by-4 sequences is the distribution of sampling time within the volume. With the interleave of 2 sequence, information near the 0 degree sampling slice is acquired early in the volume and information near the 90 degree slice is acquired at the end of the volume scan. With the interleave of 4 sequence, earlier slices are acquired near 0 degrees and 90 degrees and the latest slices are acquired around 45 degrees and 135 degrees. The distribution of any distortion in the reconstructed volume due to motion and the aggregation of samples in a volume from different times is affected by this interleave pattern. Depending on the object, the orientation of the object, and the motion patterns of the object, the distribution may produce an undesired or more desired appearance. The acquisition pattern, including number of apertures and starting orientation or locations, may be selected to produce the best image quality.

Figure 3:
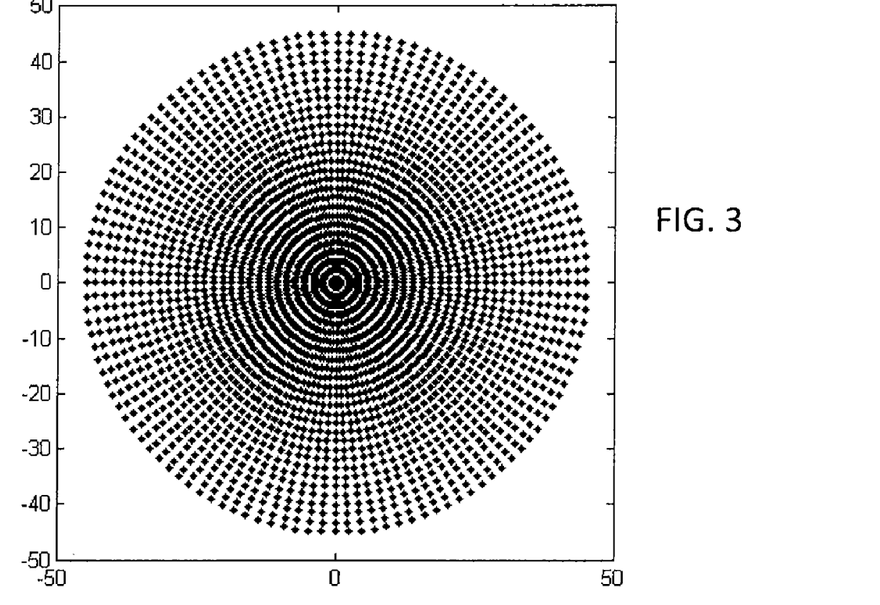
FIG. 3 is a plot of one embodiment of full scan line sampling.
Figure 4:
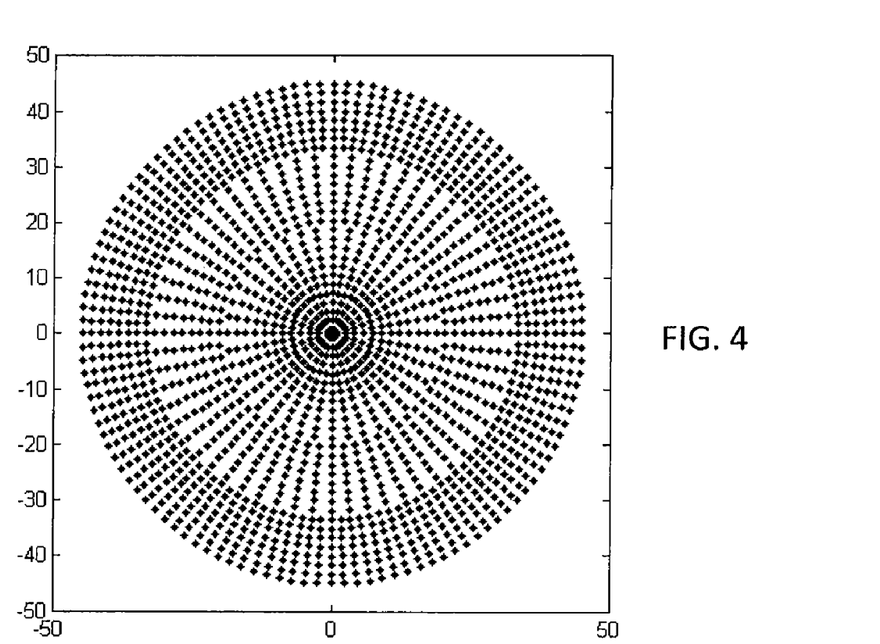
FIG. 4 is a plot of scan lines with different density according to another embodiment.

FIGS. 3 and 4 shows scan line sampling density for the 2-way and 4-way embodiments. Each dot represents a scan line distributed in the volume. FIG. 3 shows the scan line density where scan lines are evenly spaced across the planar region scanned at each aperture location or rotation. The acquisition of samples near the center of the volume of interest is relatively dense as compared to the edges. Sixty rotational angle slices with seven transmit beam groups each containing eight receive lines yields a sampling grid with 3360 lines, requiring 420 transmit events.

The frame rate may be improved by reducing the lateral sampling density for angles near the center of the scan region as compared to the scan line density away from the center. The distribution of scan lines in the volume may be made more even, such that the density is similar at the center as at the edges of the volume. Other distributions may be provided by varying the scan line density azimuthally for each aperture location.

The same variation in scan line density is used for each aperture location. Alternatively, different aperture locations use different scan line variation and/or density patterns. Different lateral scan line density is used for at least two of the different rotation angles. FIG. 4 shows variation in density by rotation angle or aperture location as well as by proximity to the center. Less scan line density is near the center than away from the center for at least one of the different aperture locations. FIG. 4 shows a grid of acquired lateral and rotational steering angles with reduced density. This reduced density uses sixty rotational angle slices, each with a number of lateral transmit events between two and seven. The outer ring contains 60 slices of 2 transmit events. The next ring contains 30 slices of 2 events. Within that are 20 slices of 2 and finally the middle contains 15 slices each with 2. The total number of transmit events is then 2×(60+30+20+15)=250 events, which is about 60% of the number in the fully sampled sequence shown in FIG. 3. The number of receive lines is 7×250=1750.

The scans for the different rings are all part of the same aperture locations or scans. In FIG. 4, the volume is divided into four concentric rings. Some aperture locations may use full sampling of scan lines azimuthally, such as every seventh or eighth rotation angle. Other aperture locations have scan lines just at the outside of the volume. Other aperture locations have scan lines at the outer portion of the volume and near the center. Other aperture locations have scan lines at the outer location of the volume, in a middle region, and not at the center. Overall, a reduced lateral scan line density is provided for the center circular region of the multidimensional array as compared to a middle circular region, and as compared to the outside circular region. The result is more even volume density of scan lines.

In the embodiment of FIG. 4, the circular rings are defined by the eight receive beams formed in response to each transmit beam. Other divisions and/or scan line patterns for a given aperture location and/or for the volume may be provided.

By reducing the lateral density for inner groups, the volume rate may be increased while not significantly reducing the overall information content of the acquired image data. Nyquist sampling is provided for the entire volume. The volume acquisition rate of the reduced density sequence using the conditions from the example of FIG. 4 may be about 20 Hz, which may be sufficient for adult cardiac imaging.

In act 44, data is received for the receive scan lines. The data is received by beamformation. Echoes impinging on the elements of the current aperture are transduced to electrical energy. The electrical energy from each element of the aperture is relatively delayed and/or weighted to beamform for a given location along each scan line. Digital and/or analog dynamic beamforming may be provided. The samples may be filtered or otherwise combined, such as for imaging at a cubic fundamental or phase inversion imaging. Any now known or later developed reception and formation of samples representing locations along one or more scan lines for each transmit event may be used.

By receiving data for each aperture, the planar or volume region is scanned. The data representing different locations within the region are provided.

In act 46, one or more samples are interpolated. For rendering or for reconstructing a plane from a volume set of data, samples along a regular grid or a reconstruction plane may be desired. The samples are created by analytic interpolation from adjacent samples. Coherent data is interpolated, such as interpolating both phase and amplitude prior to detection.

In one embodiment, samples for additional scan lines not actually received by scanning are interpolated. Additional data is interpolated for additional scan lines from the actually received data and/or other interpolated data. The interpolation may fill in or provide more even representation of a region. Interpolation allows an increase in density without reduction is frame or scan rate. Where the scan satisfies the Nyquist criteria, additional scan lines may be interpolated. Alternatively, data for less than a full scan line may be interpolated. In other embodiments, the interpolation is for reformatting the data, such as reformatting to a regular three-dimensional grid.

In act 48, the received data and/or the interpolated data are detected. Any detection process may be used. For example, the intensity of the return is detected as B-mode data. As another example, the energy (power), velocity, and/or variance of moving tissue or fluid are detected as Doppler data. Contrast agent, harmonic, or other types of detection may be provided.

Some types of detection use a plurality of samples for each spatial location. The scanning of act 42 for a given aperture location is performed multiple times to acquire the data for the detection. The repetition is performed before scanning with a different aperture and/or for a different scan line. Alternatively, the sampling for detection may be interleaved with other scans.

In act 46, an image is generated from the detected data. The data received by scanning is used to generate the image. The image represents a volume, plane or line. For two-dimensional imaging, the data may be scan converted and mapped to display values. For example, B-mode information is mapped to a gray scale and Doppler data is mapped to a color scale.

For a volume, the image is rendered from the data representing the volume. Any now known or later developed rendering may be used. For example, surface rendering or projection rendering are performed. The image is rendered as a three-dimensional representation from data for the various scan planes. Alternatively, the data from the scan planes is interpolated to a regular grid, and the image is rendered from the grid data. Shading and/or opacity weighting may be used. The data may be filtered before or after image generation.

The generation of the image occurs in real-time with the scanning. For example, the image is generated while still scanning to acquire data for subsequent images. The image is generated in a same imaging session as the acquisition. The processing delay between scanning and generating the image may be a few seconds or less, such as less than one second. In the example of FIG. 2, 3, or 4, the volume is scanned a plurality of times each second. The images are generated at the scan rate in a short time to allow processing after completion of corresponding scans of the entire volume.

In other embodiments, the data is stored. The image generation occurs from the stored data rather than being in real-time with the scanning.

Figure 5:
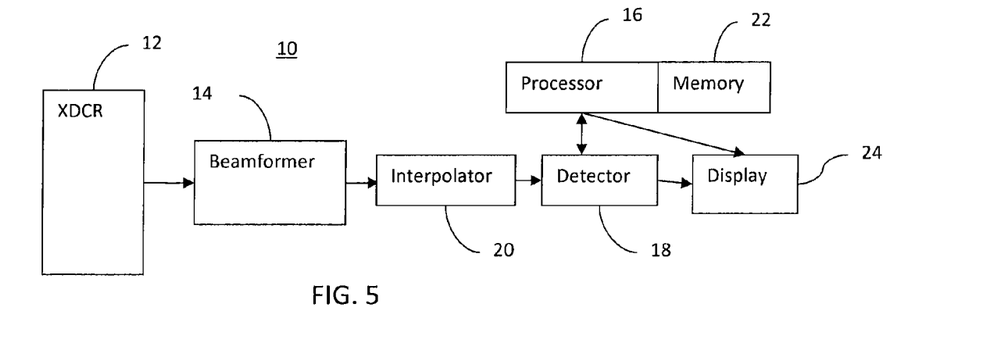
FIG. 5 is a block diagram of one embodiment of a system for scanning with ultrasound.

FIG. 5 shows a system 10 for scanning with ultrasound in medical diagnostic ultrasound. The system 10 includes a transducer 12, a beamformer 14, a processor 16, a detector 18, an interpolator 20, a memory 22, and a display 24. Additional, different, or fewer components may be provided. For example, the system 10 includes a user interface. In one embodiment, the system 10 is a medical diagnostic ultrasound imaging system. In other embodiments, the processor 16 and/or memory 22 are part of a workstation or computer different or separate from an ultrasound imaging system. The workstation is adjacent to or remote from the ultrasound imaging system.

The transducer 12 is a single element transducer, a linear array, a curved linear array, a phased array, a 1.5 dimensional array, a two-dimensional array, a radial array, an annular array, a multidimensional array, a wobbler, or other now known or later developed array of transducer elements. For example, the transducer 12 is a multi- or two-dimensional array. In one embodiment, the transducer 12 is adapted for use external to the patient, such as including a hand held housing or a housing for mounting to an external structure. As another example, the transducer 12 is a one-dimensional ring array extending continuously around a circumference of a cylinder, such as a catheter, transesophegeal probe, an endocavity probe or other probe for scanning while positioned within or in the interior of a patient.

The acoustic transducer elements of the transducer 12 are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction. All of the elements comprise a same type of material, but multiple types of acoustic transducer materials may be used for different elements. The elements have one of various possible shapes, such as triangular, rectangular, square, polygonal, circular, irregular or any combination of shapes on the face of the element or portion of the element placed adjacent a volume to be scanned.

The transducer 12 converts between electrical signals and acoustic energy for scanning a region of the patient body. The region of the body scanned is a function of the type of transducer array and position of the transducer 12 relative to the patient. For example, a linear transducer array may scan a rectangular or square, planar region of the body. As another example, a curved linear array may scan a pie shaped region of the body. Scans conforming to other geometrical regions or shapes within the body may be used, such as Vector® scans. The scans are of a two-dimensional plane. Different planes or different segments of a plane may be scanned by moving an aperture of the transducer 12. The aperture may be electronically moved without movement of the transducer 12. A volume is scanned. The volume is scanned by electronic steering alone (e.g., volume scan with a two-dimensional array), or mechanical and electrical steering (e.g., a wobbler array or movement of an array for planar scanning to scan different planes).

In one embodiment, the transducer 12 is a multi-dimensional array. The multi-dimensional transducer 12 is an array of an N by M arrangement of elements, where N and M are both greater than one. The area array sampling pattern or relative placement of one element to another element is based on any sampling method, such as a triangular grid, rectangular grid, hexagonal grid, irregular grid, or random grid. Various spacing may be provided, such as ½ or one wavelength spacing between the centers of adjacent elements. The face or surface of the entire array is square, rectangular, triangular, hexagonal, irregular, or other shape. Any of various possible multi-dimensional arrangements of elements may be used for the multi-dimensional transducer 12. The array is either flat or includes concave or convex curvature.

An electronically rotated phased array may be implemented using the multi-dimensional array of elements and an array of semiconductor or MEMS switches. The switches electronically connect elements into a phased array of elements. The elements are individual elements of the array or are formed by interconnection of a plurality of elements to form macro elements. For focal point locations over most of the depth of the beam, the macro elements may be a plurality of parallel, substantially straight lines. Where response time of switches within the electronically configurable array is sufficient, the interconnection of elements to correspond with constant delay contours dynamically changes during the reception of a beam, such as changing from concentric circular, to elliptical, and to substantially straight macro elements. Where the response time of the switches is not sufficient, the macro elements may represent a contour derived from and used for multiple focal points without any dynamic changes for a given beam. Alternatively or additionally, the macro elements are grouped, such as in rows, corresponding to different focal points. Different rows or all of the rows are used for different focal points. The macro elements are aligned in an image plane direction. By reconfiguring the macro elements, the image plane direction is rotated for scanning the three-dimensional volume. A set of rotated two-dimensional image planes are acquired as a three-dimensional data set. The rotated phased array of macro elements may be either a 1D, 1.75D or other phased array. In alternative embodiments, macro elements are not used. Instead, a 1D, 1.75D or other array is formed from elements of the multi-dimensional transducer without combining elements into macro elements.

The switches for forming the electronically rotating aperture are semiconductor switches, transistors, MEMS switches or other switches for electrically connecting or disconnecting elements and/or system channels of the beamformer 14. In one embodiment, MEMS switches comprising electrically controlled deflectable membranes or beams are used. The MEMS switches are sized so that the number of switches associated with each element covers substantially the area of the element, but other sizes may be provided. The MEMS switches are fabricated using photolithography and/or semiconductor fabrication processes allowing a large number of devices to be fabricated on a single silicon or other semiconductor chip, but two or more chips may also be used. It is also possible to include electronic circuitry and MEMS devices on the same silicon chip, allowing the switch control circuitry to be integrated with the switches on the same chip. The switches and array may be provided in a probe housing, providing a small, low cost, high yield three-dimensional imaging transducer using low power consumption, resulting in better transducer thermal efficiency. Minimal or no changes are needed in conventional system channel hardware. In another embodiment, the switches are bi-directional high-voltage switches with two pass MOSFETs, and a control for the MOSFETs where the gates float during imaging.

The switches are operable to interconnect the elements into a plurality of macro elements. Each macro element comprises at least two electrically connected elements. For example, the elements are connected in a substantially straight line, chevron patterns or in curving patterns in at least two dimensions (i.e. across the face of the transducer 14). For operation as a phased array, each macro element is continuous across the face of the two-dimensional array or a defined aperture.

The transducer 12 includes an acoustic window. The acoustic window may be an aperture or a lens. For example, a spherical lens is positioned over the face of the array. The spherical lens is used for electronic rotation of a one-dimensional array since the spherical lens always focuses the sound in the direction perpendicular to the rotated row of elements, regardless of the rotation angle.

The beamformer 14 is a transmit beamformer, receive beamformer, combinations thereof, or other now known or later developed device for scanning a region with the transducer 12. In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region.

The transducer 12 and beamformer 14 are connected together, such as the beamformer channels connecting through coaxial cables to the transducer 12. The transducer 12 and beamformer 14 are configured to scan a planar region or a segment of a planar region. The beamformer is controlled or programmed to perform the scan. The beamformer parameters, such as relative delays and/or phasing for focus, apodization, beam amplitude, beam phase, frequency, or others, are set. The aperture for transmit and the aperture for receive on the transducer 12 is set. The beamformer 14 and transducer 12 are used to generate the waveforms for the aperture and convert the waveforms to acoustic energy for transmitting the beam, and used to receive acoustic energy at the receive aperture, convert the acoustic energy to electrical energy, and beamform the received electrical signals.

Electric and/or mechanical steering may be used to scan a volume and/or plane. A volume scan may be performed using any pattern or distribution of scan lines and/or apertures. In one embodiment, an acquisition scan plane is positioned within a three-dimensional region by setting a one-dimensional aperture. Acoustic energy is transmitted in any of various now known or later developed scan patterns along the scan plane for acquiring data. The scan plane is then altered to another location in the volume by setting a different aperture.

For a given volume, the scans may be repeated. By repeating the scans, a sequence of frames of voxel data is obtained. Each frame represents the entire three-dimensional scanned volume, but may only represent smaller regions within the volume, such as a plane. By repeating the scanning, a plurality of frames of beamformed data representing the volume and/or plane within a given cycle is acquired. Any of scan line, part of frame, frame, or group of frame interleaving may be used.

The beamformer 14 is configured, using the switches in the system, switches of the transducer 12, beamformer channel selection, combinations thereof, and/or other configuration approaches to interleave two or more moving apertures on the array. The configuration is performed using hardware, software, or combinations thereof. The two moving apertures move in different directions such that adjacent locations for the moving apertures are separated by five or fewer scans using other aperture locations of the moving apertures. For example, the moving apertures use two or four one-dimensional apertures as discussed above and shown in Tables 1 and 2. The different directions are counter rotation relative to the two-dimensional array for rotation. The beamformer 14 is configured to scan different planes for the different locations of the moving apertures. Alternatively, the different directions are counter translations, such as counter translation around a ring array where each aperture location is for scanning a different segment in a plane.

For each aperture position, the beamformer 14 is configured to scan with any scan line format. In one embodiment, the scan line density changes as a function of origin, angle, aperture location, or both. For example, less scan line density occurs along a plane for scan lines in the center. Different aperture locations may scan with different densities in different locations. For example, the scan line density shown in FIG. 4 is used.

The interpolator 20 is part of the beamformer 14, the detector 18, or separate. The interpolator 20 is a memory, buffer, phase rotator, processor, adder, multipliers or other components for interpolating in-phase and quadrature or other signals with phase information. The interpolator 20 is configured as hardware, with software or combinations thereof to interpolate at least some of the data output by the beamformer 14. For example, one or more samples representing scan lines between received scan lines are interpolated. As another example, data for a scan line is replaced by interpolated data. The interpolated data is output to the detector 18. The detector 18 operates on interpolated data, actual received data, or combinations of both. In alternative embodiments, the interpolator 20 is not provided.

The detector 18 is configured to detect data output by the beamformer 14 and responsive to the moving apertures. The detector 18 is an ultrasound detector. The detector is configured by hardware and/or software to detect from the beamformed and/or interpolated data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the volume is provided. Such frames of data are provided for the same or similar volumes (e.g., similar accounts for unintended transducer and/or patient movement offsetting the volume) at different times throughout a heart cycle, over time, or merely once.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses surface rendering, projection rendering, alpha blending, texturing or other now known or later developed rendering. The data may be resampled to a regular voxel grid. Alternatively, the rendering is performed from data in a scan format, such as associated with the actual scan lines and/or interpolated scan lines. In yet other embodiments, the processor 16 is not provided or is a scan converter for generating a two-dimensional image representing a scanned plane or a reconstruction of a plane from a scanned volume.

The processor 16, the detector 18, or a separate processor generates images from the volume scan and/or plane scan or other data output from the detector 18. For example, grayscale and/or color coding is used to generate a B-mode, Doppler mode, or B-mode Doppler mode combination. Any image, such as a three-dimensional rendering, is output to the display 24.

The display 24 is a CRT, LCD, plasma, projector, printer, or other now known or later display device. The display 24 receives the image data from the processor 16 or other component and generates the image. A perfusion map, three-dimensional rendering, two-dimensional image, or other image is displayed. For example, a perfusion map is generated as a function of the detected contrast agents, such as modulating pixels by the perfusion rate for locations representing the tissue.

The memory 22 is a tangible computer readable storage medium, such as a cache, buffer, register, RAM, removable media, hard drive, optical storage device, or other computer readable storage media. The memory 22 is tangible by not being a signal, but a device. Computer readable storage media include various types of volatile and nonvolatile storage media. The memory 22 is part of the imager 17, the imaging system 16, or separate from both. The memory 22 is accessible by the processor 16.

In one embodiment, the memory 22 stores data for use by the processor 16, such as storing detected and/or image data. Additionally or alternatively, the memory 22 stores data representing instructions executable by the programmed processor 16 for scanning with ultrasound. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for scanning within a three-dimensional volume, the method comprising:
    defining a plurality of different one-dimensional apertures on a multidimensional array, each of the different one-dimensional apertures corresponding to a different rotation angle relative to the multidimensional array;
    scanning the three-dimensional volume with ultrasound sequentially from the different one-dimensional apertures at the different rotation angles; and
    performing the scanning with a counter rotation sequence of the different one-dimensional apertures corresponding to two or more rotating aperture groups of the different one-dimensional apertures sequentially rotating in opposite directions.

2. The method of claim 1 wherein the two or more rotating aperture groups comprises two aperture groups, each of the two aperture groups formed from every other one of the different one-dimensional apertures.

3. The method of claim 1 wherein the two or more rotating aperture groups comprises four aperture groups.

4. The method of claim 1 wherein scanning comprises scanning with a first time gap between scanning for sequential ones of the different one-dimensional apertures such that the scans for each adjacent one of the different one-dimensional apertures is temporally separated by two of the time gaps or less.

5. The method of claim 1 wherein scanning comprises scanning with a first time gap between scanning for sequential ones of the different one-dimensional apertures such that the scans for each adjacent one of the different one-dimensional apertures is temporally separated by four of the time gaps or less.

6. The method of claim 1 wherein scanning comprises scanning with a different lateral scan line density for at least two of the different rotation angles.

7. The method of claim 1 wherein scanning comprises scanning with reduced lateral scan line density for a first circular region closer to a center of the multidimensional array as compared to a second circular region spaced from the center by the first circular region; and further comprising interpolating additional scan lines in the first circular region.

8. The method of claim 1 further comprising:
receiving data along a plurality of scan lines;
interpolating additional data for additional scan lines from the received data; and
detecting from the data and the additional data.

9. The method of claim 1 further comprising:
generating an image as a function of data received from the scanning, wherein generating the image occurs in real-time with the scanning.

10. The method of claim 1 wherein scanning comprises scanning a plurality of planes in a volume with a two-dimensional beamformer; and further comprising rendering an image as a three-dimensional representation from data for the plurality of planes.

11. In a tangible computer readable storage medium having stored therein data representing instructions executable by a programmed processor for scanning with ultrasound, the storage medium comprising instructions for:

scanning along a plurality of scan lines in a sequence where the scan lines of the sequence form a continuous region;
forming a plurality of different apertures in an array of elements for the scanning, the different apertures corresponding to different scan lines and stepped through the continuous region such that each aperture has at least two other ones of the apertures on opposite sides; and
using an interleaved sequence of the different apertures for the scanning, the interleaved sequence stepping the different apertures in opposite directions along the array of elements through the sequence.

12. The computer readable storage medium of claim 11 wherein the array of elements comprises a one-dimensional ring array extending continuously around a circumference, and wherein using the interleaved sequence comprises stepping a first aperture clockwise around the one-dimensional ring array and stepping a second aperture counter-clockwise around the one-dimensional ring array.

13. The computer readable storage medium of claim 11 wherein the array of elements comprises a two-dimensional array, the different apertures comprising one-dimensional apertures rotated about a center of the two-dimensional array, and wherein using the interleaved sequence comprises stepping a first aperture clockwise around the center and stepping a second aperture counter-clockwise around the center.

14. The computer readable storage medium of claim 13 wherein scanning comprises scanning with less scan line density near the center than away from the center for at least one of the different apertures.

15. The computer readable storage medium of claim 14 further comprising instructions for interpolating scan line data.

16. A system for scanning with ultrasound, the system comprising:

an array of acoustic transducer elements; wherein the array comprises a two-dimensional array, the moving apertures comprise two or four one-dimensional apertures,
a beamformer connected with the array, the beamformer configured to interleave two moving apertures on the array, the two moving apertures comprising two or four one-dimensional apertures and moving in different directions comprising counter rotation relative to the two-dimensional array such that adjacent locations for the moving apertures are separated by five or fewer scans using other locations of the moving apertures;
a detector configured to detect data output by the beamformer and responsive to the moving apertures;
the beamformer configured to scan different planes for the different locations of the moving apertures;
a display configured to generate an image from the detected data and
a rendering processor configured to generate a three-dimensional rendering of a volume scanned with the different planes, the three-dimensional rendering being output to the display as the image.

17. The system of claim 16 wherein the beamformer is configured to scan with different scan line density laterally within the volume.

18. The system of claim 17 further comprising:
an interpolator configured to interpolate at least some of the data output by the beamformer and output the interpolated data to the detector.

19. The system of claim 16 wherein the array comprises a one-dimensional ring of elements around a circumference of a probe for scanning from an interior of a patient, the moving apertures comprise two or four one-dimensional apertures, the different directions comprise counter rotation around the one-dimensional ring, the beamformer configured to scan different sector segments of a plane for the different locations of the moving apertures.

* * * * *